United States Patent [19]

Jones

[11] Patent Number: 5,317,005
[45] Date of Patent: May 31, 1994

[54] PYRIMIDINYL AND TRIAZINYL HERBICIDES

[75] Inventor: Graham P. Jones, Cambridge, England

[73] Assignee: Schering Agrochemicals Limited, England

[21] Appl. No.: 966,169

[22] PCT Filed: Jul. 12, 1991

[86] PCT No.: PCT/GB91/01152

§ 371 Date: Jan. 19, 1993

§ 102(e) Date: Jan. 19, 1993

[87] PCT Pub. No.: WO92/01677

PCT Pub. Date: Feb. 6, 1992

[30] Foreign Application Priority Data

Jul. 19, 1990 [GB] United Kingdom ............. 9015916

[51] Int. Cl.$^5$ ............... C07D 239/26; C07D 401/06; A01N 43/54

[52] U.S. Cl. ................. 504/239; 504/242; 504/243; 544/319; 544/327; 544/333; 544/334; 544/335

[58] Field of Search ............ 504/239, 242, 243; 544/319, 327, 333, 334, 335

[56] References Cited

U.S. PATENT DOCUMENTS 4,962,109 10/1990 McDonald et al. ............. 544/332
5,053,072 10/1991 Ort et al. ..................... 544/327

FOREIGN PATENT DOCUMENTS 0353640 2/1990 European Pat. Off. .

*Primary Examiner*—John M. Ford
*Attorney, Agent, or Firm*—Ostrolenk, Faber, Gerb & Soffen

[57] ABSTRACT

Herbicidal pyrimidine and triazine derivatives of the formula:

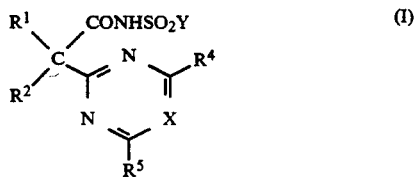

and salts thereof, where:

X represents —CH= or —N=;

Y is a substituted or unsubstituted alkyl or amino group;

$R^1$ represents a substituted or unsubstituted alkyl, cycloalkyl, phenyl or heterocyclyl group;

$R^2$ represents hydrogen, halogen or alkyl; and $R^4$ and $R^5$, which may be the same or different, each represent hydrogen, alkyl, alkoxy, amino, alkylamino, dialkylamino or halogen.

16 Claims, No Drawings

PYRIMIDINYL AND TRIAZINYL HERBICIDES

FIELD OF THE INVENTION

This invention concerns new pyrimidine and triazine derivatives having herbicidal activity, processes for their preparation, and compositions containing them.

DESCRIPTION In one aspect, the invention provides the pyrimidine and triazine derivatives of the formula:

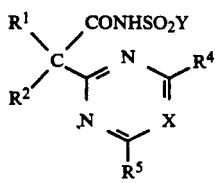

and salts thereof, where:

X represents —CH' or —N=;
Y is a substituted or unsubstituted alkyl or amino group;
$R^1$ represents a substituted or unsubstituted alkyl, cycloalkyl, phenyl or heterocyclyl group;
$R^2$ represents hydrogen, halogen or alkyl; and
$R^4$ and $R^5$, which may be the same or different, each represent hydrogen, alkyl, alkoxy, amino, alkylamino, dialkylamino or halogen.

Any alkyl moiety present in the molecule is preferably of 1 to 6 carbon atoms, especially of 1 to 4 carbon atoms. Specific preferred unsubstituted alkyl groups include methyl, ethyl, n-propyl, isopropyl, n-butyl and t-butyl.

When Y represents a substituted alkyl group, it may be substituted for example by one or more halogen atoms (eg fluorine, chlorine or bromine atoms), by cyano, by alkoxy of 1 to 4 carbon atoms (eg methoxy or ethoxy), or by a group —COZ, where Z is a group —NR'R" or —OR' in which R' and R" each represent hydrogen or a substituted or unsubstituted alkyl or phenyl group.

When $R^1$ represents a substituted alkyl group, it may be substituted for example by one or more halogen atoms (eg fluorine, chlorine or bromine atoms), by cyano, by phenyl, by alkoxy of 1 to 4 carbon atoms (eg methoxy or ethoxy), or by a group —COZ, where Z is a group R', —NR'R" r —OR' in which R' and R" each represent hydrogen or a substituted or unsubstituted alkyl or phenyl group.

When $R^1$ represents a cycloalkyl group, it is preferably of 3 to 7 carbon atoms, especially cyclopentyl or cyclohexyl, and is desirably unsubstituted.

When $R^1$ represents a substituted phenyl group, it is preferably substituted by one or more halogen atoms, eg fluorine, chlorine or bromine, nitro groups, substituted or unsubstituted amino groups (eg alkylamino, dialkylamino or acylamino groups, especially where the alkyl moiety has from 1 to 4 carbon atoms), cyano groups, alkyl or alkoxy groups of 1 to 4 carbon atoms (eg methyl, ethyl, methoxy or ethoxy), alkoxycarbonyl groups in which the alkyl moiety is of 1 to 4 carbon atoms (eg methoxycarbcnyl or ethoxycarbonyl), or phenoxy groups.

When $R^1$ represents a heterocyclyl group, it is preferably of 5 or 6 ring atoms, at least one of which is desirably sulphur, oxygen or nitrogen. Preferred such heterocyclic groups include furyl, pyridyl and, especially, thienyl groups. Specific preferred groups are 2-furyl, 2-pyridyl and, particularly, 2-thienyl. If desired, the heterocycle may be substituted, for example by one or more alkyl groups of 1 to 4 carbon atoms.

When $R^2$, $R^4$ or $R^5$ represents halogen, it is preferably fluorine, chlorine or bromine.

The salts of the compounds of formula I are preferably those formed on the nitrogen atom of the sulphonylamino group with an alkali-metal or ammonium cation, eg sodium, potassium, or isopropylammonium.

Specific preferred groups which $R^1$ may represent include ethyl, n-propyl, isopropyl, s-butyl, 3,3-dimethyl-2-oxcbutyl, 1,3,3-trimethyl-2-oxobutyl, dimethylcarbamcylmethyl, 1-(methoxycarbonyl)el--hyl, 1-(t-butyloxycarbonyl)ethyl, 1-(dimethylcarbamoyl)ethyl, 1-phenylethyl, cyclohexyl, phenyl, 2-chlorophenyl, 3-chlorophenyl, 2-cyanophenyl, 3-triflucromethylphenyl, 2-methylphenyl, 3-methylphenyl, 4-aminophenyl, 2-methoxyphenyl, 3-methoxyphenyl, 2-methoxycarbonylphenyl, 2-ethoxycarbonylphenyl and 2-thienyl.

Specific preferred groups which $R^2$ may represent include hydrogen, methyl, ethyl, n-propyl and isopropyl.

Specific preferred groups which Y may represent include methyl, cyanomethyl, chloromethyl, trifluoromethyl and dimethylamina.

Specific groups which $R^4$ and $R^5$ may represent include methylamino, dimethylamino and, more preferably, methyl, methoxy and chloro.

In a particularly preferred group of compounds of formula I, Y represents methyl, $R^1$ represents isopropyl or phenyl, $R^2$ represents hydrogen, and $R^4$ and $R^5$ both represent methoxy.

Specific preferred compounds according to the invention are those of the Examples provided hereinafter.

In another aspect, this invention provides a process for the preparation of a pyrimidine or triazine derivative of formula I, in which a compound of the formula:

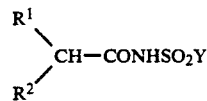

where $R^1$, $R^2$ and Y are as defined hereinbefore is reacted in the presence of a base, and in an appropriate solvent medium, with a pyrimidine or triazine of the formula:

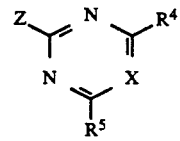

where Z is a leaving group, particularly chloro or a group of formula $R^aSO_2$— where $R^a$ is alkyl of 1 to 4 carbon atoms, and X, $R^4$ and $R^5$ are as defined hereinbefore to give the desired compound.

The base employed is preferably an alkali-metal hydride, for example sodium hydride, in a suitable solvent, for example dimethylformamide, and at temperature of from 0° C. to 25° C. Alternatively, the reaction may be carried out using butyllithium and di-isopropylamine at a temperature of about −70° C.

In another aspect the invention provides a process for the preparation of a pyrimidine or triazine derivative of formula I where $R^1$ is a substituted or unsubstituted alkyl group and $R^2$ is hydrogen, in which a compound of the formula:

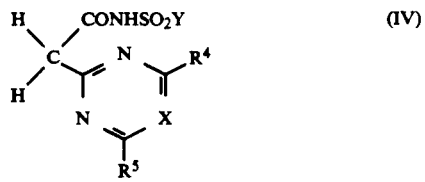

(IV)

where X, Y, $R^4$ and $R^5$ are as defined hereinbefore is alkylated in the presence of a strong base to give the desired compound.

The alkylation may be effected by means of a suitable alkylating agent, for example the appropriate alkyl halide.

The base employed is preferably butyllithium, and the reaction is desirably effected at a temperature of about $-70°$ C. in an inert solvent such as tetrahydrofuran.

The compounds of formula IV may themselves be prepared by a process in which a pyrimidinyl- or triazinylacetic acid of the formula:

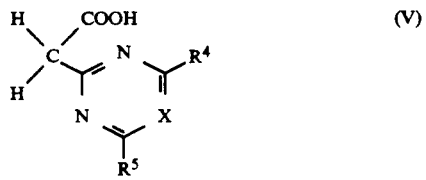

(V)

where X, $R^4$ and $R^5$ are as defined hereinbefore is reacted with a sulphonamide of the formula $YSO_2NH_2$ where Y is as defined hereinbefore, in the presence of 1,1'-carbonyldiimidazole, to give the desired compound.

The reaction is preferably effected at a temperature of from 0 to 50° C., and in an inert solvent medium such as tetrahydrofuran.

Some compounds of formula I can of course be converted into other compounds of formula I by methods known per se. For example, the compounds where $R^2$ represents hydrogen can be converted into corresponding compounds where $R^2$ is halogen or alkyl by conventional halogenation or alkylation processes.

The salts of the compounds of formula I may be prepared from the corresponding unsalified compounds of formula I by salt-forming processes known per se. Thus, for example, the compound of formula I may be reacted with a suitable base containing or giving rise to the desired cation.

The compounds of formula I and their salts are herbicidally-active against a wide range of broad-leaved and grassy weeds, but are comparatively safe to certain crop species. They may thus be of use as herbicides, and especially as selective herbicides, particularly in the control of a range of weeds in cereals or other crops, eg wheat, rice, barley, maize, soya beans, oilseed rape, cotton or sugar beet.

In another aspect, therefore, this invention provides a method of combating weeds at a locus infested or liable to be infested therewith which comprises applying thereto an effective amount of one or more compounds of formula I or salts thereof as defined hereinbefore.

Preferred rates of application are from 0.1 to 2kg/ha, especially from 0.5 to 1.5 kg/ha.

In a further aspect, this invention provides a herbicidal composition which comprises one or more compounds of formula I or salts thereof in association with a suitable carrier and/or surface active agent.

The compositions of the invention usually contain from 0.01 to 99% by weight of the present compounds, and are normally produced initially as concentrates containing from 0.5 to 99%, preferably from 0.5 to 85%, and especially from 10 to 50% by weight thereof. Such concentrates are diluted if necessary before application to the locus to be treated such that the active ingredient comprises from 0.01 to 5% by weight of the formulation applied.

The carrier may be water, in which case an organic solvent may also be present, though this is not usually employed. A flowable suspension concentrate may be formed by grinding the compound with water, a wetting agent and a suspending agent, e.g. xanthan gum.

The carrier may alternatively be a water immiscible organic solvent, e.g. a hydrocarbon which boils within the range 130–270° C., e.g. xylene, in which the compound is dissolved or suspended. An emulsifiable concentrate containing a water immiscible solvent may be formed with a surface ac-live agent so that the concentrate acts as a self-emulsifiable oil on admixture with water.

The carrier may alternatively be a water-miscible organic solvent e.g. 2-methoxy ethanol, methanol, propylene glycol, diethylene glycol, diethylene glycol monoethyl ether, methylformamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, e.g. a polyhalogenated alkane such as dichlorofluoromethane, and suitably also with a solvent.

The term 'surface active agent' is used in the broad sense to include materials variously called emulsifying agents, dispersing agents and wetting agents. Such agents are well known in the art.

The surface active agents used may comprise anionic surface active agents, for example mono- or diesters of phosphoric acid with a fatty alcohol ethoxylate, or salts of such esters, fatty alcohol sulphates such as sodium dodecyl sulphate, ethoxylated fatty alcohol sulphates, ethoxylated alkylphenol sulphates, lignin sulphates, petroleum sulphonates, alkylaryl sulphonates such as alkyl-benzene sulphonates or lower alkylnaphthalene sulphonates, salts of sulphonated naphthaleneformaldehyde condensates, salts of sulphonated phenolformaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise non-ionic agents, for example condensation products or fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5,-decyn-4,7-diol, or ethoxylated acetylenic glycols.

The surface active agents may also comprise cationic agents, for example alkyl- and/or aryl-substituted quaternary ammonium compounds such as cetyl trimethylammonium bromide, or ethoxylated tertiary fatty amines.

Preferred surface active agents include ethoxylated fatty alcohol sulphates, lignin sulphonates, alkyl-aryl sulphonates, salts of sulphonated naphthalenefcrmaldehyde condensates, salts of sulphonated phenolformaidehyde condensates, sodium oleoyl N-methyltauride, dialkyl sulphosuccinates, alkyl phenol ethoxylates, and fatty alkyl ethoxylates.

The present active compounds may be admixed with another pesticide, eg a herbicide, fungicide or insecticide, or a plant growth regulator, particularly another herbicide. Suitable further herbicides include trietazine, linuron, MCPA, dichlorprop, isoxaben, diflufenican, metolachlor, fluometuron, oxyfluorfen, fomesafen, bentazone, prometryne, norflurazon, chlomazone, EPTC, imazaquin, and especially isoproturon, methabenzthiazuron, trifluralin, ioxynil, bromoxynil, benazolin, mecoprop, fluroxypyr, alachlor, acifluorfen, lactofen, metribuzin, pendimethalin, ethofumesate, benfuresate, phenmedipham, benzophenap, butachlor, chlomethoxyfen, dimepiperate, mefenacet, molinate, naproanilide, oxadiazon, piperophos, prometryne, pyrazoxyfen, pyrazosulfuron-ethyl, bensulfuron, simetryne, pyrazolate, pretilachlor, thiobencarb and pyributicarb.

The present compound may be applied to plants, the soil, land or aquatic areas, and particularly to a locus at which a crop is growing. The compounds are particularly active preemergence, but also have post-emergence activity.

EXAMPLES

The invention is illustrated by the following Examples in which Me=methyl, Et=ethyl, Pr=propyl, Bu=butyl, Cyhex=cyclohexyl, Ph=phenyl and Th=2-thienyl.

EXAMPLE 1

2-(4,6-Dimethoxypyrimidin-2-yl)-N-(methylsulphonyl)-2-(2-thienyl)acetamide n-Butyllithium (20ml of a 2.5M solution in hexane) was added to a stirred solution of N-(methylsulphonyl)-2-(2-thienyl)acetamide (4.67g) in dry tetrahydrofuran (60ml) at −70° C. under nitrogen. The solution was stirred at room temperature for 2 hours, and was then cooled to −70° C., after which 4,6-dimethoxy-2-methylsulphonyl pyrimidine (3.45g) was added, and the resulting suspension was allowed to warm to room temperature. The reaction mixture was stirred overnight, then the solvent was evaporated and the residue treated with water (100 ml) . The insoluble material was removed by washing with ether (50ml). Acidification of the aqueous solution with hydrochloric acid gave an oil which was extracted into ethyl acetate (2×50ml). The combined extracts were dried and evaporated to give a brown oil, which was purified by chromatography to give 1.8g of the desired product, mp 96–97° C.

EXAMPLE 2

2-(4 6-Dimethoxypyrlmidin-2-(2-thienyl)acetamide isopropylamine salt

Isopropylamine (0.11 g) was added to a stirred solution of the product of Example 1 (0.6g) in ethyl acetate (10ml) at room temperature. After stirring for 10 minutes, hexane (15ml) was added dropwise, and the resulting solid was filtered off and dried to give 0.5g of the desired isopropylamine salt, mp 110–111° C.

EXAMPLES 3–25

The following compounds of formula I in which $R^2$ is hydrogen and $R^4$ is methoxy were prepared by methods analogous to those of Examples 1 or 2:

| Ex | $R^1$ | $R^5$ | X | Y | M Pt (°C.) |
|---|---|---|---|---|---|
| 3 | i-Pr | OMe | CH | Me | 111–112 |
| 4 | n-Pr | OMe | CH | Me | 89–91 |
| 5 | Ph | OMe | CH | Me | 130–132 |
| 6 | Ph | OMe | N | Me | 151–152 |
| 7 | Th | Cl | CH | Me | 172–175 |
| 8 | i-Pr | OMe | CH | $CH_2Cl$ | 125–126 |
| 9 | i-Pr | OMe | N | Me | 119–122 |
| 10 | i-Pr | Cl | CH | Me | 150–153 |
| 11 | 3-ClPh | OMe | CH | Me | 103–108 |
| 12 | i-Pr | Cme | CH | Et | 130–131 |
| 13 | i-Pr | OMe | CH | n-Pr | 93–94 |
| 14 | i-Pr | OMe | CH | i-Pr | 116–117 |
| 15 | i-Pr | OMe | CH | $NMe_2$ | 111–112 |
| 16 | Cyhex | OMe | CH | Me | 124–126 |
| 17 | Isopropylamine salt of Ex 5 | | | | 150–152 |
| 18 | Diethylamine salt of Ex 5 | | | | 102–106 |
| 19 | Cyclohexylamine salt of Ex 5 | | | | 141–144 |
| 20 | Cyhex | OMe | CH | Et | 108–110 |
| 21 | s-Bu | OMe | CH | Me | 94–95 |
| 22 | Ph | OMe | CH | $NMe_2$ | Oil |
| 23 | i-Pr | OMe | N | i-Pr | 125–127 |
| 24 | i-Pr | OMe | N | Et | 91–94 |
| 25 | i-Pr | OMe | N | Me | Oil |

EXAMPLE 26

2-(4,6-Dimethoxypyrimidin-2-yl)-5,5-dimethyl-N-(methylsulphonyl)-4-oxohexanamide (a) (4,6-dimethoxypyrimidin-2-yl)acetic acid n-Butyllithium (200 ml of 2N in pentane) was added dropwise over 30 minutes to a stirred solution of di-iso-propylamine (40.4 g) in tetrahydrofuran (200 ml) at −70° C. under nitrogen. The mixture was stirred for 20 minutes and then 4,6-dimethoxy-2-methylpyrimidine (61.6 g) in tetrahydrofuran (200 ml) was added dropwise over 20 minutes. The mixture was stirred at −70° C. for 30 minutes before being poured onto a large excess of solid carbon dioxide. The mixture was allowed to warm to room temperature before water (800 ml) was added. The clear solution was concentrated to half volume under vacuum and was then washed with ether. The aqueous phase was acidified with concentrated hydrochloric acid and the resulting solid was filtered, washed with water and dried to give 58.3 g of (4,6-dimethoxypyrimidin-2-yl)acetic acid.

(b) 2-(4,6-Dimethoxypyrimidin-2-yl)-N-(methtlsulphonyl) acetamide

The product of stage (a) (11.89 g) was added to a solution of 1,11-carbonyldiimidazole (10.79 g) in dry tetrahydrofuran (150ml) at room temperature under nitrogen to give a pale yellow solution which was stirred at room temperature for one and a half hours. Methanesulphonamide sodium salt (14.05 g) was added in one portion to give a light brown suspension which was stirred at room temperature for 3 days. The solvent was evaporated, and the residue was treated with water to give a cloudy solution. This was washed with ether (2×150 ml) and then acidified to pH=1 with 2N hydrochloric acid. The resulting solution was extracted with ethyl acetate (3×150 ml), and the combined extracts were washed with saturated sodium chloride solution, dried, and evaporated to give a white solid. Recrystallisation from ethyl acetate gave 7.7 g of the desired product as white crystals, mp 135–136° C.

(c) 2-(4,6-Dimethoxypyrimidin-2-yl)-5,5-dimethyl-N-(methylsulphonyl)-4-oxohexanamide The product of stage (b) (2.75 g) was stirred under nitrogen in tetrahydrofuran (50 ml) at −70°C. n-Butyllithium (8 ml of a 2.5M solution in hexane) was added dropwise over 5 minutes to give a white suspension which was allowed to warm to room temperature, and was stirred for 3 hours before cooling to −75° C. A solution of 1-bromo-3,3-dimethyl-2-butanone (1.79 g) in tetrahydrofuran (30 ml) was added dropwise, and the mixture was stirred for 2 hours before warming to room temperature. After stirring overnight, the mixture was added to water (100 ml), and was washed with ether (2×100 ml). The aqueous solution was acidified to pH=1 with 2N hydrochloric acid to give an oil which was extracted with ether (3×100 ml). The combined extracts were washed with saturated sodium chloride solution (100 ml), dried and evaporated to give a yellow oil (2.31 g) which was purified by chromatography and recrytallisation from diisopropyl ether to give 1.2 g of the desired product as a white solid, mp 97°–98° C.

EXAMPLES 27–32

The following compounds of formula I in which $R^2$ is hydrogen, $R^4$ and $R^5$ are methoxy, X is CH, and Y is methyl were prepared by methods analogous to that of Example 26:

| Ex | $R^1$ | M Pt (°C.) |
|---|---|---|
| 27 | t-BuCOCHMe | 132–135 |
| 28 | Me$_2$NCOCH$_2$— | 188–190 |
| 29 | MeOCOCHMe | 183–185 |
| 30 | t-BuOCOCHMe | 113–120 |
| 31 | Me$_2$NCOCHMe | 182–183 |
| 32 | PhCHMe | 139–140 |

HERBICIDAL EXAMPLE A (Pre-Emergence)

Seeds of the weed species listed below were sown in anodised aluminium pans 19 cm long×9.5 cm wide×6 cm deep, containing sterilized sandy loam. They were watered and then sprayed with the compounds of the Examples listed below formulated as a solution/suspension in 1:1 by volume of acetone and the wetting agent polyoxyethylene (20 mols) monolaurate solution (2 g per liter).

The concentration of each test compound and volume of application were calculated to give the desired rate of application of the compound in 450 litres per hectare. After 3 to 4 weeks growth in the controlled environment room (20° C.; 75–95% relative humidity; 14 hours per day artificial illumination) the plants were visually assessed for any herbicidal response.

All differences from an untreated control were scored accordingly to an index where 0=no effect, 1=1–24% effect, 2=25–69% effect, 3=70–89% effect and 4=90-14 100% effect. In the table below, the following letters are used to denote the plant species:

a—*Alopecurus myosuroides* (blackgrass)
b—*Avena fatua* (wild oat)
c—*Agropyron repens* (Couchgrass)
d—*Bromus steriles* (sterile brome)
e—*Viola arvensis* (field pansy)
f—*Stellaria media* (chickweed)
g—*Galium aparine* (cleavers)
j—*Matricaria spp* (mayweed)
k—*Polygonum lapathifolium* (Pale persicaria)
l—*Veronica persica* (speedwell).

The results obtained were as follows:

| Ex | Kg/ha | a | b | c | d | e | f | g | j | k | l |
|---|---|---|---|---|---|---|---|---|---|---|---|
| 1 | 0.25 | 2 | 0 | 2 | 0 | 2 | 3 | 3 | 2 | 3 | 4 |
| 2 | 0.5 | 3 | 1 | 2 | 0 | 3 | 4 | 3 | 3 | 4 | 4 |
| 3 | 0.125 | 3 | 3 | 4 | 3 | 2 | 3 | 3 | 4 | 4 | — |
| 4 | 0.125 | 3 | 3 | 4 | 2 | 2 | 3 | 2 | 2 | 4 | — |
| 5 | 0.125 | 3 | 2 | 4 | 2 | 2 | 3 | — | 2 | 3 | 3 |
| 9 | 0.5 | 4 | 4 | 4 | — | 4 | 4 | 4 | 3 | 4 | 4 |
| 10 | 0.5 | 3 | 2 | 4 | — | 3 | 1 | 3 | 2 | 3 | 3 |
| 11 | 0.25 | 2 | 4 | 2 | — | 3 | 3 | 4 | 3 | 3 | 4 |
| 12 | 0.25 | 2 | 2 | 2 | 2 | — | 2 | 2 | 2 | 3 | 3 |
| 13 | 0.5 | 2 | 1 | 3 | 0 | 3 | 2 | 3 | 4 | 3 | 4 |
| 14 | 0.5 | 2 | 2 | 3 | 1 | 3 | 2 | 4 | 2 | 3 | 3 |
| 15 | 0.25 | 2 | 2 | 2 | 0 | 2 | 3 | 3 | 0 | 3 | 4 |
| 16 | 0.5 | 2 | 2 | 3 | 2 | 2 | 3 | 2 | 3 | 3 | 3 |
| 17 | 0.25 | 3 | 2 | 4 | 2 | 3 | 4 | 3 | 3 | 4 | 4 |
| 18 | 0.25 | 2 | 2 | 4 | 2 | 3 | 4 | 3 | 4 | 4 | 4 |
| 19 | 0.25 | 3 | 2 | 4 | 2 | 2 | 3 | 3 | 3 | 4 | 4 |
| 21 | 0.25 | 4 | 3 | — | 3 | 3 | 4 | 4 | 4 | 4 | 4 |
| 22 | 0.25 | 3 | 2 | 4 | 2 | 3 | 4 | 3 | 3 | 4 | 4 |

HERBICIDAL EXAMPLE B (Post-Emergence)

Seeds of the plant spec listed above were sown in anodised aluminium pans, 19 cm long×9.5 cm×6 cm deep, containing sterilised sandy loam. They were then watered and placed in a controlled environment room (20° C.; 75-95% relative humidity; 14 hours per day artificial illumination). Fourteen or twenty one days after sowing (depending on the species but when most plants had 2 to 3 true leaves) the seedlings received a foliar spray of the compounds of the Examples listed below, formulated as a solution/suspension in 1:1 by volume of acetone and the wetting agent polyoxyethylene (20 mols) monolaurate solution (2 g per liter).

The concentration of each test compound was calculated to give the desired rate of application of the compound in 450 liters per hectare. After 2 to 3 weeks growth in the controlled environment room the plants were visually assessed for any herbicidal response.

All differences from an untreated control were scored according to an index where 0=no effect, 1=1–24% effect, 2=25–69% effect, 3=70–89% effect and 4=90–100% effect. In the table below, the letters used denote the same plant species as in Herbicidal Example A:

The results obtained were as follows:

| Ex | Kg/ha | a | b | c | d | e | f | g | j | k | l |
|---|---|---|---|---|---|---|---|---|---|---|---|
| 1 | 0.25 | 2 | 0 | 1 | 0 | 2 | 3 | 4 | 3 | 2 | 3 |
| 2 | 0.25 | 2 | 2 | 0 | 0 | 2 | 4 | 3 | 2 | 2 | 2 |

-continued

| Ex | Kg/ha | a | b | c | d | e | f | g | j | k | l |
|---|---|---|---|---|---|---|---|---|---|---|---|
| 3 | 0.25 | 3 | 3 | 3 | 2 | 3 | 3 | 4 | 3 | 2 | — |
| 5 | 0.25 | 3 | 4 | 3 | 2 | 2 | 4 | 3 | 3 | 4 | — |
| 8 | 0.5 | 2 | 2 | 0 | 0 | 2 | 2 | 3 | 2 | 2 | 2 |
| 10 | 0.25 | 2 | 3 | 2 | 3 | 1 | 2 | 3 | 3 | 2 | 2 |
| 11 | 0.25 | 2 | 2 | 2 | 2 | 2 | 4 | 3 | 3 | 3 | 3 |
| 12 | 0.25 | 3 | 2 | 2 | 0 | 2 | 2 | 3 | 2 | 2 | 2 |
| 13 | 0.5 | 2 | 2 | 1 | 2 | 2 | 1 | 3 | 3 | 2 | 2 |
| 14 | 0.5 | 3 | 2 | 0 | 0 | 2 | 2 | 3 | 3 | 2 | 2 |
| 15 | 0.25 | 2 | 2 | 1 | 2 | 2 | 2 | 3 | 3 | 3 | 2 |
| 16 | 0.5 | 2 | 2 | 2 | 1 | 2 | 2 | 2 | 2 | 2 | 1 |
| 18 | 0.25 | 2 | 3 | 4 | 2 | 2 | 4 | 4 | 3 | 3 | 3 |
| 19 | 0.25 | 2 | 2 | 2 | 2 | 2 | 4 | 4 | 3 | 3 | 3 |
| 21 | 0.5 | 4 | 4 | 3 | 3 | 4 | 4 | 4 | 4 | 4 | 4 |
| 22 | 0.25 | 3 | 3 | 3 | 2 | 3 | 4 | 4 | 3 | 4 | 3 |

I claim:
1. A pyrimidine derivative of the formula:

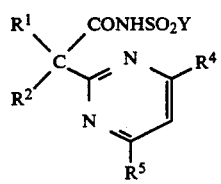

and salts thereof, where:

Y is an alkyl group of 1 to 6 carbon atoms which is unsubstituted or is substituted by one or more halogen atoms, by cyano, by alkoxy of 1 to 4 carbon atoms, or by a group —COZ in which Z is a group —NR'R" to —OR' and R' and R" each represent hydrogen, alkyl of 1 to 6 carbon atoms, or phenyl; or is an amino group;

$R^1$ is substituted or unsubstituted alkyl group of 1 to 6 carbon atoms as defined above for Y; cycloalkyl group of 3 to 7 carbon atoms; phenyl which is unsubstituted or substituted by one ore more halogen atoms, nitro groups, amino groups, alkylamino, dialkylamino or acylamino groups where the alkyl moieties have from 1 to 4 carbon atoms, cyano groups, alkyl or alkoxy groups of 1 to 4 carbon atoms, alkoxycarbonyl groups in which the alkyl moiety is of 1 to 4 atoms, or phenoxy groups; or a heteocyclyl group selected from furyl, pyridyl and thienyl which is unsubstituted or substituted by one or more alkyl groups of 1 to 4 carbon atoms;

$R^2$ is hydrogen, halogen, or alkyl of 1 to 6 carbon atoms; and $R^4$ and $R^5$, which may be the same or different, are each hydrogen, alkyl of 1 to 6 carbon atoms, alkoxy of 1 to 6 carbon atoms, amino, alkylamino of 1 to 6 carbon atoms, dialkylamino in which each alkyl moiety is of 1 to 6 carbon atoms, or halogen.

2. A compound according to claim 1 in which Y represents said substituted or unsubstituted alkyl.

3. A compound according to claim 2 in which Y represents methyl, cyanomethyl, chloromethyl, trifluoromethyl or dimethylamino.

4. A compound according to claim 1 in which $R^1$ represents ethyl, n-propyl, isopropyl, s-butyl, 3,3-dimethyl-2-oxobutyl, 1,3,3-trimethyl-2-oxobutyl, dimethyl-carbamoylmethyl, 1-(methoxycarbonyl)ethyl, 1-(t-butoxycarbonyl)ethyl, 1-(dimethylcarbamoyl)ethyl, 1-phenylethyl, cyclohexyl, phenyl, 2-chlorophenyl, 3-chlorophenyl, 2-cyanophenyl, 3-trifluoromethylphenyl, 2-methylphenyl, 3-methylphenyl, 4-amino-phenyl, 2-methoxyphenyl, 3-methoxyphenyl, 2-methoxycarbonyl-phenyl, 2-ethoxycarbonylphenyl or 2-thienyl.

5. A compound according to claim 1 in which $R^2$ represents hydrogen, methyl, ethyl, n-propyl or isopropyl.

6. A compound according to claim 1 in which $R^4$ and $R^5$ are each methyl, methoxy or chloro.

7. A herbicidal composition which comprises from 0.01 to 99% by weight of one or more compounds according to claim 1, in association with a suitable carrier and/or surface active agent.

8. A method of combating weeds which comprises applying to a locus infested or liable to infestation therewith an effective amount of one or more compounds according to claim 1.

9. A compound according to claim 4 in which Y represents methyl, cyanomethyl, chloromethyl, trichloromethyl or dimethylamino; $R^2$ represents hydrogen, methyl, ethyl, n-propyl or isopropyl; and in which $R^4$ and $R^5$ are each methyl, methoxy or chloro.

10. A compound according to claim 9 in which $R^1$ is an unsubstituted group selected from the group consisting of alkyl, cycloalkyl, phenyl and thienyl; $R^2$ is hydrogen; $R^4$ and $R^5$ are both methoxy; and Y is methyl or dimethylamino.

11. A compound according to claim 10 in which Y is methyl and $R^1$ is isopropyl or phenyl.

12. A herbicidal composition which comprises a herbicidally effective amount of at least one compound according to claim 9 and a herbicidally acceptable carrier.

13. A herbicidal composition which comprises a herbicidally effective amount of at least one compound according to claim 10 and a herbicidally acceptable carrier.

14. A herbicidal composition which comprises a herbicidally effective amount of at least one compound according to claim 11 and a herbicidally acceptable carrier.

15. A method of combating weeds which comprises applying to a locus infested or liable to infestation therewith an effective amount of one or more compounds according to claim 9.

16. A method of combating weeds which comprises applying to a locus infested or liable to infestation therewith an effective amount of one or more compounds according to claim 10.

* * * * *